United States Patent [19]

Buxton

[11] 3,960,140
[45] June 1, 1976

[54] PHYSIOLOGICAL MONITORING SYSTEM

[76] Inventor: Richard L. Buxton, 11406 Hillwood Dr., S.E., Huntsville, Ala. 35803

[22] Filed: Feb. 18, 1971

[21] Appl. No.: 116,588

[52] U.S. Cl. .................... 128/2.06 R; 128/2.06 B
[51] Int. Cl. ............................................ A61b 5/04
[58] Field of Search ................ 128/2.06 A, 2.06 B, 128/2.06 E, 2.06 F, 2.06 G, 2.06 R, 2.06 V, 2.1 A, 2.1 E, 2.1 R

[56] References Cited
UNITED STATES PATENTS

| | | | |
|---|---|---|---|
| 3,212,496 | 10/1965 | Preston | 128/2.1 A |
| 3,506,813 | 4/1970 | Trimble | 128/2.1 R |
| 3,602,222 | 8/1971 | Herndon | 128/2.06 F |

*Primary Examiner*—William E. Kamm
*Attorney, Agent, or Firm*—C. A. Phillips

[57] ABSTRACT

A physiological measurement system for electrically sensing heart activity of a plurality of patients and providing on a single display tube, divided into sections, one for each patient, composite displays consisting of an ECG waveform, a digital readout of heart rate, and permissible heart rate limits indicated by markers between which a heart rate marker is relatively positioned in terms of its value and the value of the limits.

1 Claim, 8 Drawing Figures

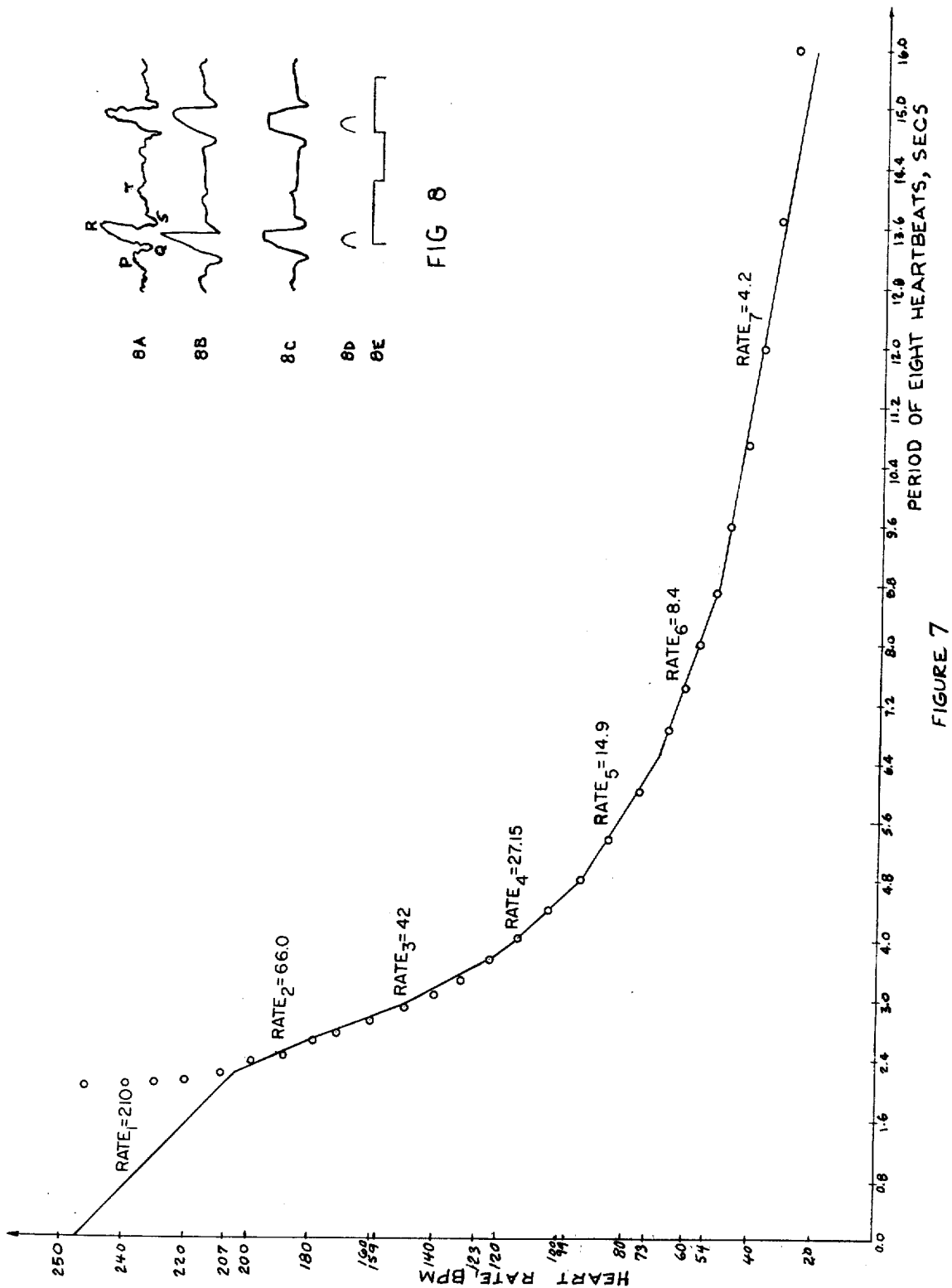

PHYSIOLOGICAL MONITORING SYSTEM

This invention relates to physiological measurement systems and particularly to a system for measuring and displaying data indicative of body functions such as the function of the heart.

It is well established that the heart provides electrical signals representative of its operation and it is acknowledged that apparatus has heretofore been constructed to detect and display these signals, particularly in the form of graphic displays, usually referred to as electrocardiograms or ECG or EKG. The technique generally employed involves placing on the body at spaced points two or more electrodes which pick up electrical signals which are a function of heart activity. A variation of this technique involves placing a patient on a floating platform and obtaining electrical signals from accelerometers which measure accelerations of the body produced by heart action. The signals obtained by one of these techniques are amplified, processed variously, and presented as waveforms on a cathode ray tube or on some form of graphic recorder. One typical use of ECG waveforms is for the monitoring of heart patients in intensive care and coronary care units in hospitals. It is this usage and application of electrical indications of heart activity whether ECG or ballistocardiogram to which the present invention is particularly directed. Monitoring by observation of ECG waveforms in an intensive care or coronary care unit typically involves the monitoring of a cathode ray display for each of several patients. Normally the nurse, intern or doctor in attendance would be charged with the care of several patients wired for such displays which means, of course, that while attention is divided between the several patients, at the same time the observer must be able to recall or remember data history and critical data for each patient. Critical data includes the magnitude of the ECG waveform, lower permissible heart rate and upper permissible heart rate. Accordingly, it is to be appreciated that it is a significant undertaking to be mindful of the critical factors as relate to a single patient and difficult to the point of being hazardous for a single observer to be significantly mindful of such factors for several patients.

Another and related problem is that of providing apparatus for accurately indicating heart rate without waiting for a substantial number of heart beats, often requiring time that can not be afforded if heart rate changes are rapid and wherein treatment to be effective must be rapidly applied. For example, heart rate, as is well known, is given in heart beats per minute, thus if each heart beat is accurately recognized and accurately counted for a minute of time, an accurate figure of heart rate will be thus obtained. This, however, involves one or more difficulties. First, in the case of many critically ill patients a minute is too long to wait to obtain a heart rate, and second, due to the complex action of the heart, it is often difficult to detect and distinguish distinct heart beats, and third, as a combination of the first two factors, where a lesser period of counting is used, say 15 seconds, and the results multiplied by four to obtain a heart rate, frequently the results now obtained are off as much as one beat every 15 seconds and thus four beats in a computed heart rate in beats per minute. If any smaller period of time of counting is attempted, with presently known equipment, this error is further magnified. Such errors too frequently arise and for such reasons as illustrated by the following example: assume in a given case that counting is for 15 seconds and during this time 14 beats are registered, but these 14 beats occur in 14 seconds and a 15th beat has not yet occurred but is just about to occur. It may be that the 15th beat will occur within a few microseconds. Thus, you can readily see that there is indicated essentially a one beat error or essentially a four beat error in heart rate. Another problem considered by this invention relates generally to the detection, amplification and processing of physiological signals wherein, in the past, results have often been erratic because of a variety of problems, including electrical interference and varying levels of input signals with different patients and sometimes with the same patient.

Still another problem considered by this invention relates generally to the accuracy of physiological monitoring systems and particularly to the accuracy of displays used to display heart data. A typical difficulty is that of determining with existing equipment whether, for example, an unusual or unanticipated indication is a result of equipment misadjustment or failure or actually represents a patient's condition.

Accordingly, it is an object of this invention to provide a heart monitoring system with which a medical observer with a minimum of training can monitor conditions of several patients without the necessity of having to remember a substantial amount of critical data and thus to substantially reduce the problem of human error in monitoring heart patients.

It is still another object of this invention to provide a more accurate system of detection of a common point on each heart cycle whereby heart beats can be more accurately identified and indicated.

It is still another object of this invention to provide a system of heart rate measurement which will provide improved accuracy while at the same time reducing the necessary period of observation for the measurement, thus providing additional and valuable time for treatment after a critical condition has been detected.

It is a still further object of this invention to provide a multiple patient monitoring system wherein the whole system, and particularly the display system, functions in a manner wherein faulty readings resulting from equipment malfunction will be more readily detectable as such and thus more readily distinguishable from the condition of a patient.

BRIEF DESCRIPTION OF DRAWINGS

FIG. 1b is an electrical schematic diagram of a patient sensor-telemetry transmitter employed in the system.

FIG. 4 illustrates a series of waveforms pertinent to the operation of the data processing unit shown in FIG. 3.

FIG. 7 is a graph illustrating the characteristics of operation of certain of the rate circuitry illustrated in FIG. 6.

FIG. 8 illustrates in graphical form the treatment of certain waveforms pertinent to the operation of rate circuitry shown in FIG. 6.

Referring now to FIG. 1 there is generally shown the measurement system of this invention which broadly includes identical remote patient measurement units P1, P2, P3 and P4, one for each patient monitored by this system, and central monitor 28. The patient units are affixed to the body of patients who may be in the same room or in differnt rooms. Referring to patient measurement unit P1, input probes or electrodes 30, 32 and 34 are of the type adapted to make good electrical contact with the body of a patient. Heart developed signals sensed by probes 30, 32 and 34, provide an electrically balanced input signal between probes 30 and 32 with respect to probe 34. They are preamplified in signal amplifier 36, conditioned in signal conditioner 38, translated from analog to digital form in A to D converter 40 and transmitted by transmitter 42 via antenna 44 to central monitor 28. Logic generator 46 provides certain pulse data to amplifier 36 and *a* to *d* converter 40 for appropriately forming data as will be explained.

Figure 1:
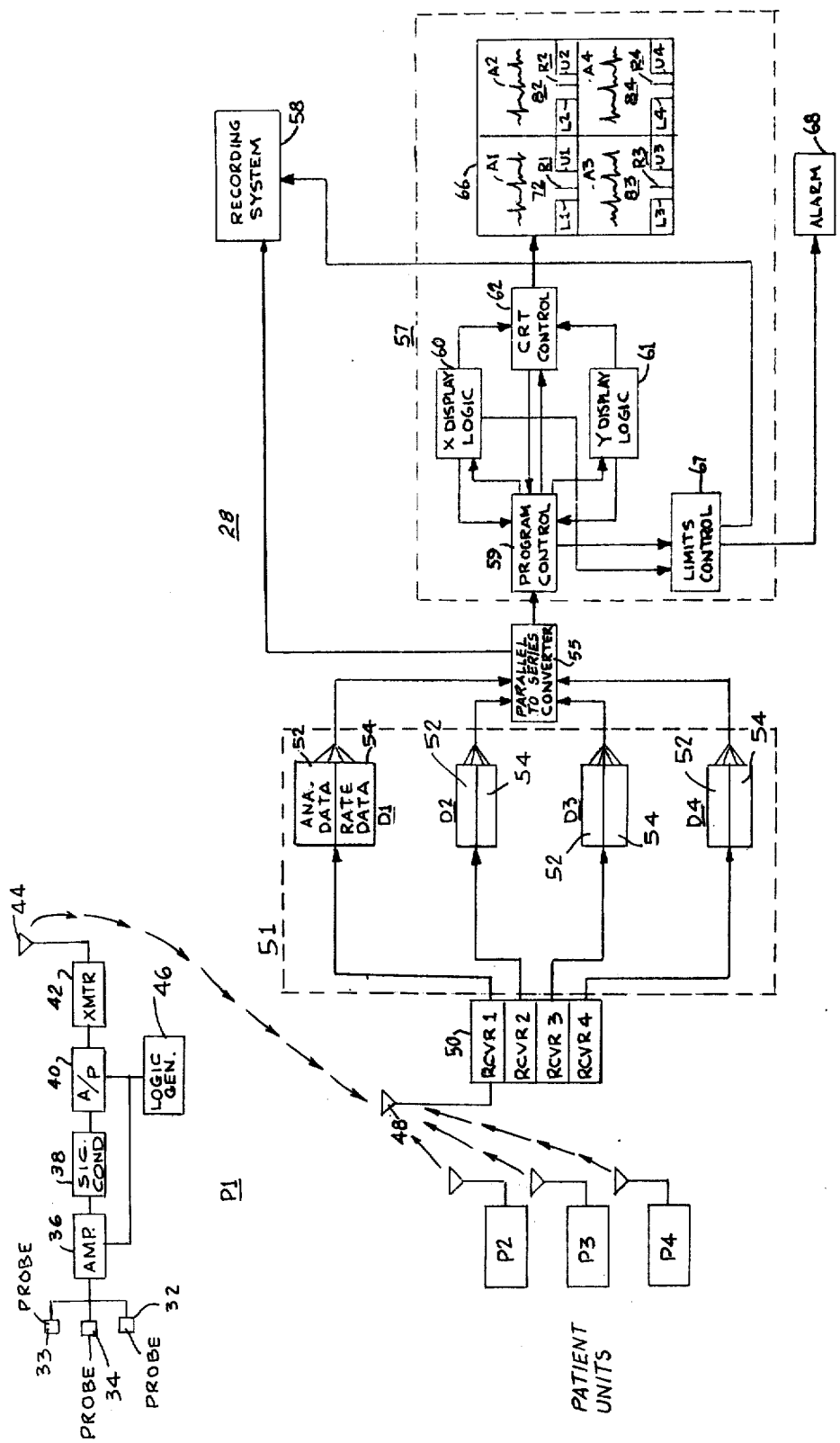
FIG. 1 is an electrical block diagram of the overall system of the invention.
Figure 2:
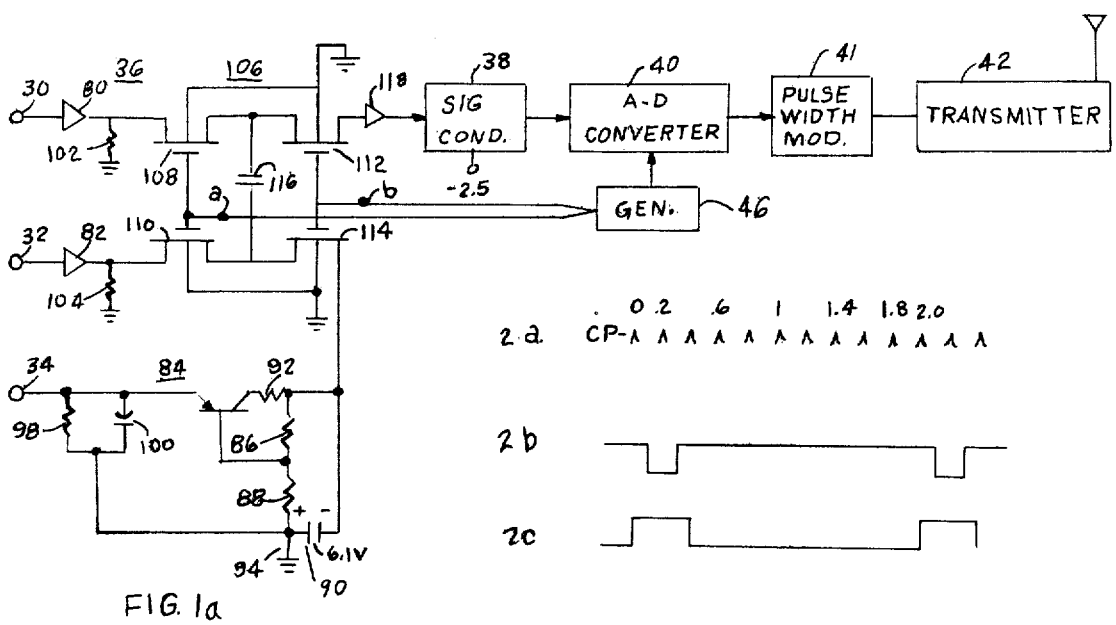
FIG. 2 illustrates a series of waveforms pertinent to the operation of the sensor-telemetry transmitter of the sensor-telemetry transmitter shown in FIG. 1b.

The link from transmitter 42 of each of the patient units is typically by radio and typically utilizes VHF or UHF range and employs pulse modulation. The data is received by antenna 48 and fed to receivers RCV1, RCV2, RCV3 and RCV4 of receiver unit 50, each receiver being tuned to receive only one of a transmitted signal from a patient unit, the signal carriers from the different patient units being sufficiently spaced from one another in frequency to prevent interference.

The discrete outputs from receivers RCV1, RCV2, RCV3 and RCV4 are fed, respectively, to data processor 51. It consists of data development and detector circuits D1, D2, D3 and D4, respectively, generally referred to hereinafter as data detector D1–D4, one for each patient. Each data detector includes an analog or ECG data detector 52 and heart rate detector 54. Analog detector 52 functions to recreate and temporarily store digitized incremental values of ECG activity of a patient and heart rate detector 54 detects, from an output of analog detector, or analog data detector 52, heart rate for a particular patient. The outputs of data processor 51 are fed through parallel to series convertor 55 to display 57 and recording system 58. It is to be noted that the data words are originally received in series, or in serial form, then translated into parallel form by the data detectors and after the data is processed it is supplied to the display and recording system in serial form.

Program control 59 of display 57 controls the flow of analog and rate data from data processor 51. It supplies analog data to Y display logic 61, rate data to X display logic 60 and supplies certain constants to X display logic 60 and Y display logic 61 as will be further explained. Program control 59 also affects central control over cathode ray tube control 62, which directly controls cathode ray tube 66 and limits control 67 which indicates and controls recording system 58 and alarm 68 in accordance with detection of a heart rate condition which is out of a predetermined and preset range set into the equipment.

As shown, cathode ray tube or display 66 displays ECG data for four patients, together with heart rate. Heart rate is presented both in digital form, shown, and an analog presentation in which vertical lines L1, L2, L3 and L4 are positioned horizontally at a position representative of a lower heart rate limit and vertical lines U1, U2, U3 and U4 are horizontally positioned in terms of an upper preset heart rate limit. Vertical lines R1, R2, R3 and R4 are horizontally positioned to correspond to actual heart rate and thus an observer can readily note not only the actual heart rate, which is digitally presented but its relationship to predetermined values which the patient's physician has determined as representative of critical limits. Thus the observer may readily note a changing condition of a patient as an analog rate line approaches one of the limits and take appropriate action. In addition, the system provides for automatic recording when one of these limits is reached as well as to sound alarm 68.

As shown, the indicated heart rate for Patient 1, or R1, is 72 beats per minute, for Patient 2 or R2, is 82 beats per minute, for Patient 3, or R3, is 83 beats per minute, and for Patient 4, or R4, is 84 beats per minute.

Waveform A1 is representative of the ECG waveform for Patient 1, waveform A2 is representative of the ECG waveform for Patient 2, waveform A4 is representative of the ECG waveform for Patient 3, and waveform A4 is representative of the ECG waveform for Patient 4.

FIG. 1*b* shows a combined schematic and block diagram of one of the patient units P1-P4. Amplifier 36 comprises preamplifiers 80 and 82 which initially amplify the signals picked up between probes 30 and 34 and 32 and 34, respectively.

As a feature of this invention electrode 34 provides a reference potential of minus 3.0 volts to the body by means of voltage regulator 84. Voltage regulator circuit 84 employs a voltage divider which consists of resistors 86 and 88 in its collector-base circuit. This voltage divider is supplied 6.1 volts from battery 90. Collector current is reduced to a desired limit by collector resistor 92. The divided and stabilized emitter-base voltage created thereby appears between system ground terminal 94 and the emitter of transistor 96 across resistor 98 and capacitor 100. Electrodes 30, 32 and 34 are appropriately spaced on the body of a patient to provide, in effect, differential inputs to preamplifiers 80 and 82 and provide amplified inputs across resistors 102 and 104 with respect to ground. The composite differential input thus obtained avoids common signal problems such as 60 cycle hum, but without the necessity of separate plus and minus power supplies, the minus 3.0 volts reference to the body as illustrated makes this unnecessary.

The outputs of preamplifiers 80 and 82 are fed to sample and hold circuit 106 which performs two functions. First, this circuit translates the two input signals from a differential form to a single ended form, and second, this circuit develops a series of discrete, single value, outputs which are thus in a form suitable for digital encoding. The sample and hold circuit is constructed and functions as follows. Four M.O.S. solid state switches 108, 110, 112 and 114 serve to alternately charge capacitor 116 to the composite of the input voltages and to apply the thus charged output of capacitor 116 to the input of amplifier 118. Switches 108 and 110 serve as input switches and are simultaneously closed by negative keying pulses for a 0.2 millisecond duration as shown in waveform 2b. Overlapping in time output switches 112 and 114 are opened for a 0.4 millisecond by the absence of keying pulse as shown in waveform 2c. This is the charging or "sample" mode. Next, with switches 108 and 110 open for 1.8 milliseconds and switches 112 and 114 closed by a keying pulse for 1.6 milliseconds the output of capacitor 116, which represents a sampled bit or portion of ECG data, is applied to the input of amplifier 118. The keying pulses are generated in logic generator 46, which basically generates clock pulses CP shown in waveform 2a, which occur each 0.2 milliseconds or at the rate of 5,000 pulses per second.

In operation, switches 112 and 114 open, then 0.1 milliseconds later, switches 108 and 110 close to permit capacitor 116 to be charged to some input potential value which is representative of the sum of the outputs of amplifiers 80 and 82. The charging or sampling time is 0.2 seconds and at the end of this period switches 108 and 110 open. Next, and 0.1 millisecond later, switches 112 and 114 are operated closed for the "readout" period which lasts 1.6 milliseconds and during this period one end of capacitor 116 is referenced to signal round and the other end connected as a single ended input to amplifier 118. Thus the sum of the reference bias and capacitor potential as represented by pulse shown in waveform 2d is applied to amplifier 118 for a 1.6 millisecond period.

The total signal amplification of the input circuitry is divided between preamplifiers 80 and 82 and amplifier 118 with an approximate gain of 25 being obtained in preamplifiers 80 and 82 and a gain of 40 being obtained in amplifier 118 for a total gain of 1,000. By dividing the total gain in this manner substantial latitude in signal levels can be tolerated without circuit overloading of the sample and hold circuitry.

The output of amplifier 118 is fed to signal conditioner 38, which adds a −2.5 volts to signals to change the signal range to one of one polarity as shown in waveform 2e to facilitate analog to digital conversion. Thus signals which previously ranged between −2.5 and +2.5 volts now range in value from 0 to −5.0 volts. Waveform 2e illustrates a case where the signal is near maximum in negative direction. The output of signal conditioner 38 is fed to analog to digital convertor 40 which encodes each input pulse into an eight bit binary code as illustrated in waveforms 2f 2g and 2h. Waveform 2f is illustrative of the binary code representative of the value indicated by waveform 2e. Waveform 2h illustrates the binary code placed in a pulse duration code with a short pulse illustrative of a zero and a long pulse illustrative of a "one." In the code employed the first bit has the most significant value and bit eight has the least significant value. As an example the data is coded as follows:

| Bit | Voltage |
|---|---|
| 1. | 2.560 |
| 2. | 1.280 |
| 3. | 0.640 |
| 4. | 0.320 |
| 5. | 0.160 |
| 6. | 0.080 |
| 7. | 0.040 |
| 8. | 0.020 |

The output of analog to digital convertor 40 is fed to digital to pulse width modulator 41 in which the binary coded words shown in waveform 2h are combined with synchronizing pulses S1 and S2 as shown in waveform 2g and transmitter 42 modulated in frequency having a first value in frequency when the waveform of waveform 2g has a zero value and a secondary frequency when it has a plus value. It is to be noted that the synchronizing pulses are intermediate in width when compared with a "zero" bit pulse and "one" bit pulse. The total number of bits per word in the transmitted code is thus 10 bits and the purposes of the added synchronizing pulses is to indicate that good data appears between successive sets of such pulses. They have a pulse width of 0.1 milliseconds.

The output of transmitter 42 is coupled to antenna 44 for transmission of its modulated output to central monitoring system 28 (FIG. 1).

The transmissions from patient units P1–P4 received by receiver assembly 50 which includes four FM receivers RCV1, RCV2, RCV3 and RCV4, each being tuned to the separate frequency of one of the four patient transmitters. The output of each receiver is fed to a corresponding data processor D1–D4 and for purposes of illustration, data processor D1 is shown and described more particularly.

Analog detector 52 decodes and makes available for display, ECG data and heart detector 54 computes and makes available for display heart rate data. ECG data is also supplied by analog detector 52 through parallel to series data word converter 55 to recorder or recording system 58 for selective recording of ECG data from any one of four patients.

Figure 3:
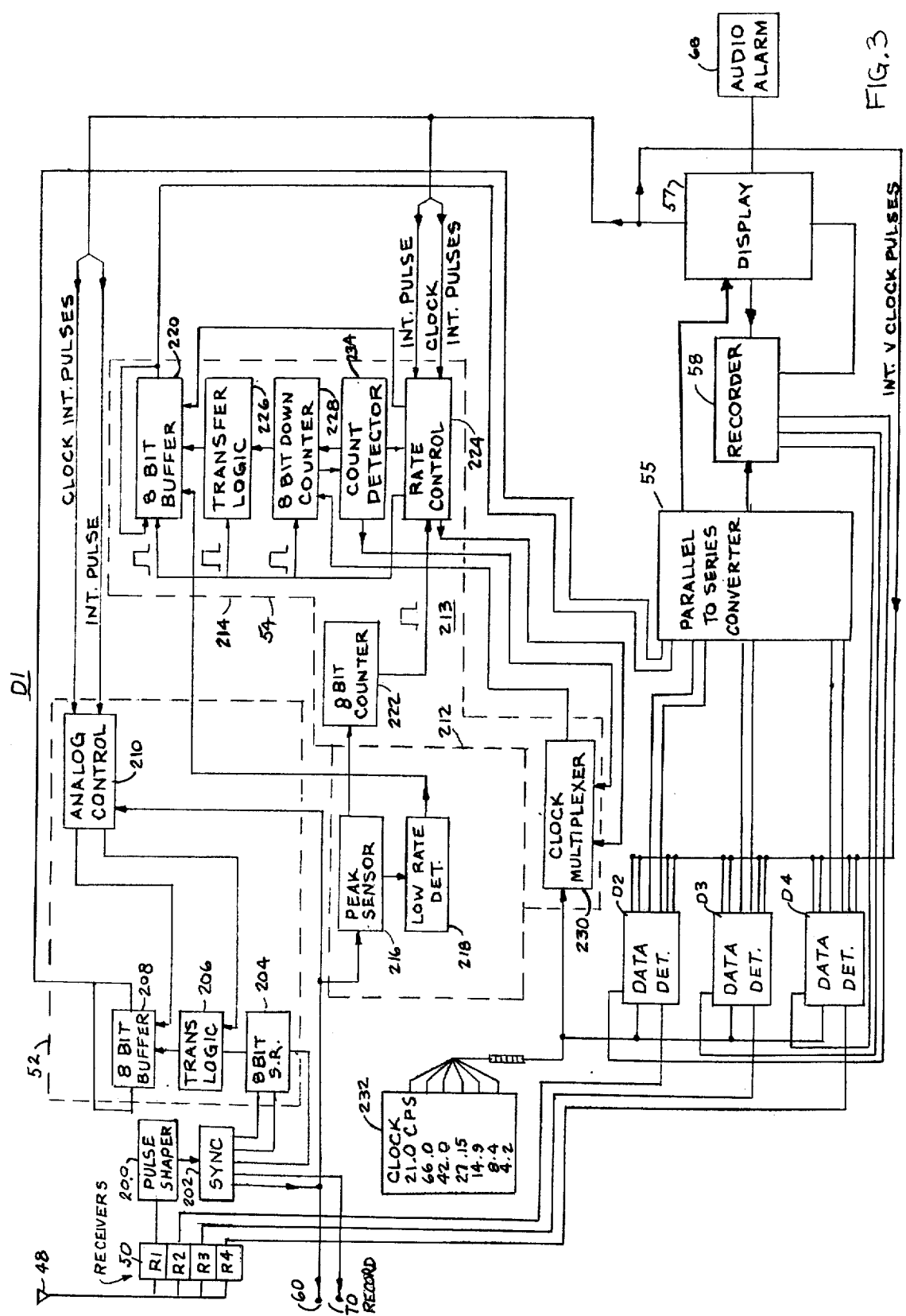
FIG. 3 is an electrical block diagram of the central monitor of this invention, showing in some detail certain of the data processing units employed.

Referring now to FIG. 3 and particularly to data detector D1, an output from receiver RCV1 is fed to pulse shaper 200 which functions to clean up the demodulated output of the receiver RCV1 and to provide a pulse train as shown in waveform 4a corresponding to the original waveform which was used to modulate transmitter 42. This data is fed to synchronizer 202 which performs several functions. One, it detects and forms clock pulses as shown in waveform 4b which consists of one pulse for each bit of data, plus a pulse for each of the two synchronizing pulses. Thus, valid bits of data are identified as eight data pulses preceded by and followed by two synchronizing pulses.

Synchronizer 202 also breaks out the eight bits of data making up a data word which would simply be the presence of the pulse when a "one" is present and no pulse when a "zero" is to be represented corresponding to the eight bit positions of the binary word and supplies the binary word to shift register 204 and to recorder or recording system 58. A further function of synchronizer 202 is to develop and provide up-date pulses as shown in waveform 4c. These update pulses occur coincident with the trailing edge of pulse No. 10 of a word provided these conditions have been satisfied: there has preceded a complete set of data bits, that is bits 1–8; that pulses 9 and 10 have been particularly identified as being sync pulses having the requisite width; and, that preceding these data bits of the word there has occurred sync pulses 9 and 10 of the previous word.

By placing these requirements on the derivation of up-date pulse U it is assured that this pulse will not occur if the data word which proceeds it is incomplete, that is represents bad data. The duration of an up-date pulse U is 3 microseconds.

Figure 5:
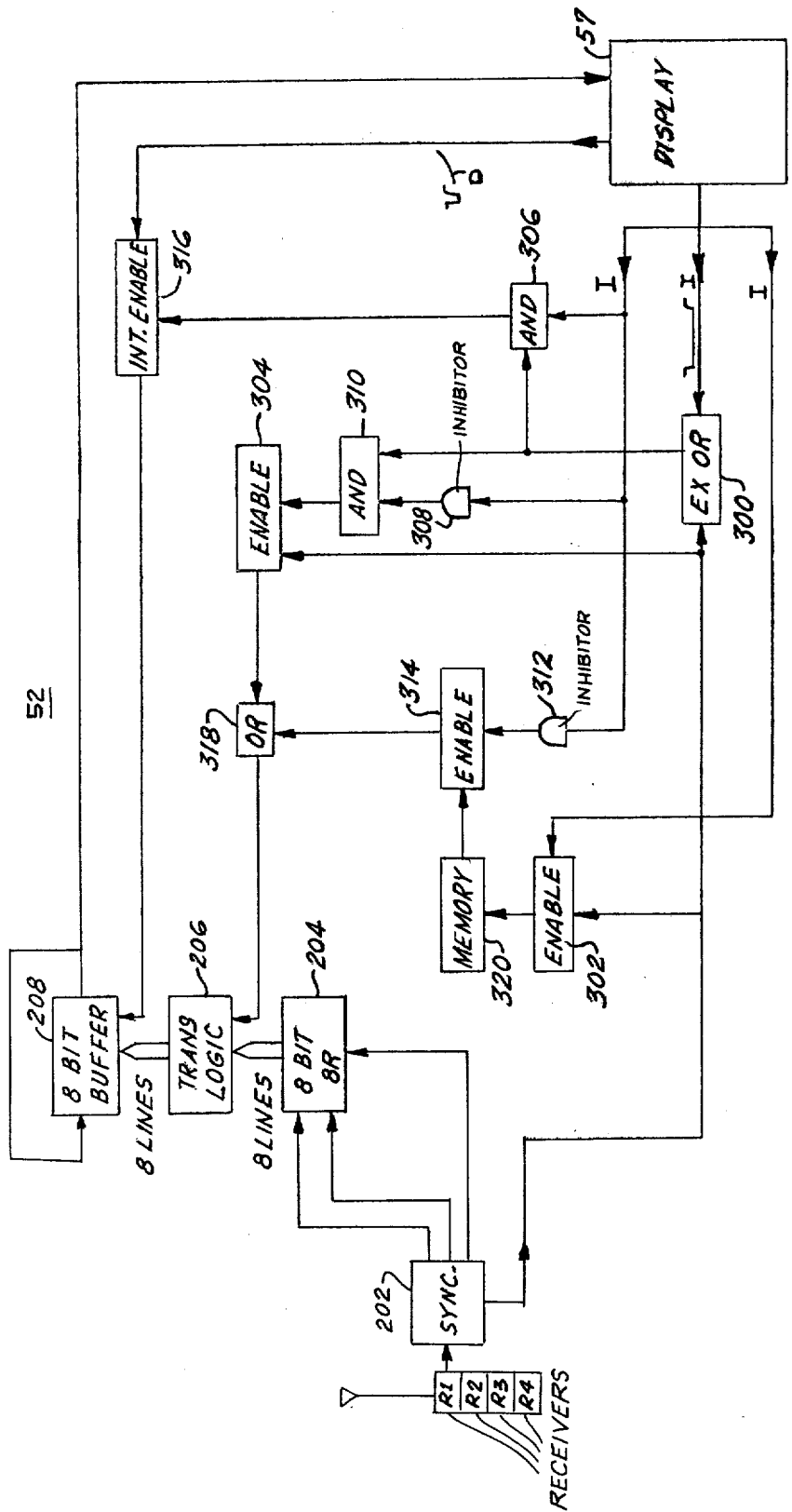
FIG. 5 is an electrical block diagram of that portion of the central monitor particularly relating to the processing of ECG data.

Analog detector 52, shown in FIG. 5 consists basically of eight bit shift register 204, transfer logic circuit 206, eight bit buffer or storage register 208 and analog control circuit 210. Analog detector 52 converts serially incoming data words into parallel form, selectively stores them, and supplies these words through parallel to series converter 55, which converts them back to serial form, on command to display 57. As a particular feature of this invention, the rate of acceptance of data by buffer 208 and the rate of supplying it to display 57 are independent and no necessary synchronization of supply and demand is necessary. To accomplish this, analog detector 52 provides for a system of non-interfering up-date of data from shift register 204 to buffer 208 and readout of data from buffer 208. This is accomplished as follows: at the end of each data word, synchronizer 202 provides an up-date pulse U (FIG. 5) and this pulse is supplied to analog control 210. Analog control 210 is further supplied with interrogate pulse I shown in waveform 4d from display 57. Each time that display 57 requests new data it sends out, concurrently with the interrogate pulse U, a set of eight clock pulses D shown in waveform 4e and FIG. 5. Interrogate pulse I is applied to one input of Exclusively OR gate 300 (FIG. 5) and up-date pulses U (waveform 4c) are supplied to the other input. Up-date pulses U are also supplied to enable circuits 302 and 304. Interrogate pulses are also supplied to one input of AND gate 306, and through inhibitor 308 to one input of AND gate 314. Display clock pulses D (waveform 4e) consists of bursts of eight pulses falling within the period of interrogate pulse I (4d) and which commence 6 microseconds after the initiation of interrogate pulse I. In examining the waveforms it is to be appreciated that there is no fixed relation between the occurrence of the pulses in waveform 4a, 4b and 4c and pulses shown in waveforms 4d and 4e. The display clock pulses are provided as an input to interrogate enable circuit 312. If an interrogate pulse I should arrive from display 57 at any time between the occurrence of successive up-date pulses U, no interferring problem arises and thus the operation of analog detector 52 is as follows. With only interrogate pulse I applied to EXCLUSIVELY OR gate 300, it will appear at the output of EXCLUSIVELY OR gate 300 and be applied to one input of AND gate 306. Inhibitor 308 prevents it from being applied to AND gate 314. Interrogate pulse I is also applied to an input of AND gate 306 which in turn provides an enable input to interrogate enable 312 to permit the passage of a burst of eight clock pulses D from display 57 to eight bit buffer 208 which causes stored data representing the last data word received to clock out to display 57. Eight bit buffer 208 is of the non destructive type and its output is fed back into its input to retain the data in the buffer pending an up-date, receipt of a new data word, as will be further explained.

We will next assume a condition wherein there is an interference or overlap between the occurrence of an interrogate pulse I and an up-date pulse U wherein the up-date pulse is received first. Thus, up-date pulse U is applied to one input of EXCLUSIVELY OR gate 300 at a time when no interrogate pulse I is applied to the other input. Thus up-date pulse U would appear as an output of EXCLUSIVELY OR gate 300 to AND gates 306 and 314. Initially and before an interrogate pulse is applied to inhibitor 308, AND gate 314 is operated and in turn so is enable circuit 302 to permit up-date pulse U to pass through OR gate 316 and then on to transfer logic 206, which passes the data bits present in eight bit shift register 204 to buffer 208. This requires only three microseconds and thus it will be noted that this up-date will be completed prior to the occurrence of the first of the eight clock-out pulses D inasmuch as there is a 6 microsecond time lapse after the beginning of an interrogate pulse I before the first clock pulse, and we have stated that the up-date pulse is 3 microseconds in duration and commenced prior to the interrogate pulse.

Now to further illustrate that the up-date sequence does not interfere with the process of clock out of data from storage register 208, it is to be noted that as soon as the interrogate pulse does arrive, and the up-date pulse ends, EXCLUSIVELY OR circuit 300 is operated. This causes AND gate 306 to be operated and in turn operates interrogate enable circuit 316 so that clock pulses are premitted through enable circuit 316 to buffer 208 and data is clocked out to display 57. However, since there is the 6 microsecond delay between the arrival of the interrogate pulse and bursts of the clock pulses, clock out can occur only after up-date has been completed. We will now assume the third possible condition and that is where interrogate pulse I has arrived first and up-date pulse U arrives sometime after and during interrogate pulse I. Initially, and with only interrogate pulse I present, an output of EXCLUSIVELY OR circuit 300 is applied to AND gate 306 and AND gate 310. Inhibitor circuit 308 is also energized and it prevents the operation of AND gate 310 to disable enable circuit 304 and thus block the normal passage of an up-date pulse through OR gate 318 to transfer logic 206, and thus interference between up-date and clock-out when the up-date pulse does arrive. Instead, the up-date pulse is routed through enable circuit 314, which is enabled by interrogate pulse I, to memory circuit 320. Memory circuit 320 holds an up-date voltage for a period just extending beyond the period of the interrogate pulse.

For the balance of time of interrogate pulse I and with interrogate pulse I being the only input to EXCLUSIVELY OR gate 300, inhibitor 312 prevents the operation of enable circuit 322 and any readout of the up-date pulse from memory circuit 320 to operate transfer logic 206. At the end of interrogate pulse I, and with no input to EXCLUSIVELY OR gate 300, inhibitor 312 is no longer energized and enable circuit 314 is energized to pass the up-date pulse from memory circuit 320 and be passed through OR gate 318 to transfer logic 206 to accomplish up-date. In the meantime, and during interrogate pulse I, interrogate enable circuit 316 is operated by AND gate 306 and display clock pulses D are fed to shift register 208 and data words stored therein are clocked out to display 57.

Thus, in instances where an interrogate pulse requesting data occurs first, and up-date pulse indicating time for up-dating of data occurs during the interrogating pulse, up-dating is inhibited during the interrogated period but is accomplished immediately at the end of the interrogate period. Thus there is no loss of ECG data, up-dating occurring once for each new word of data received.

Figure 6:
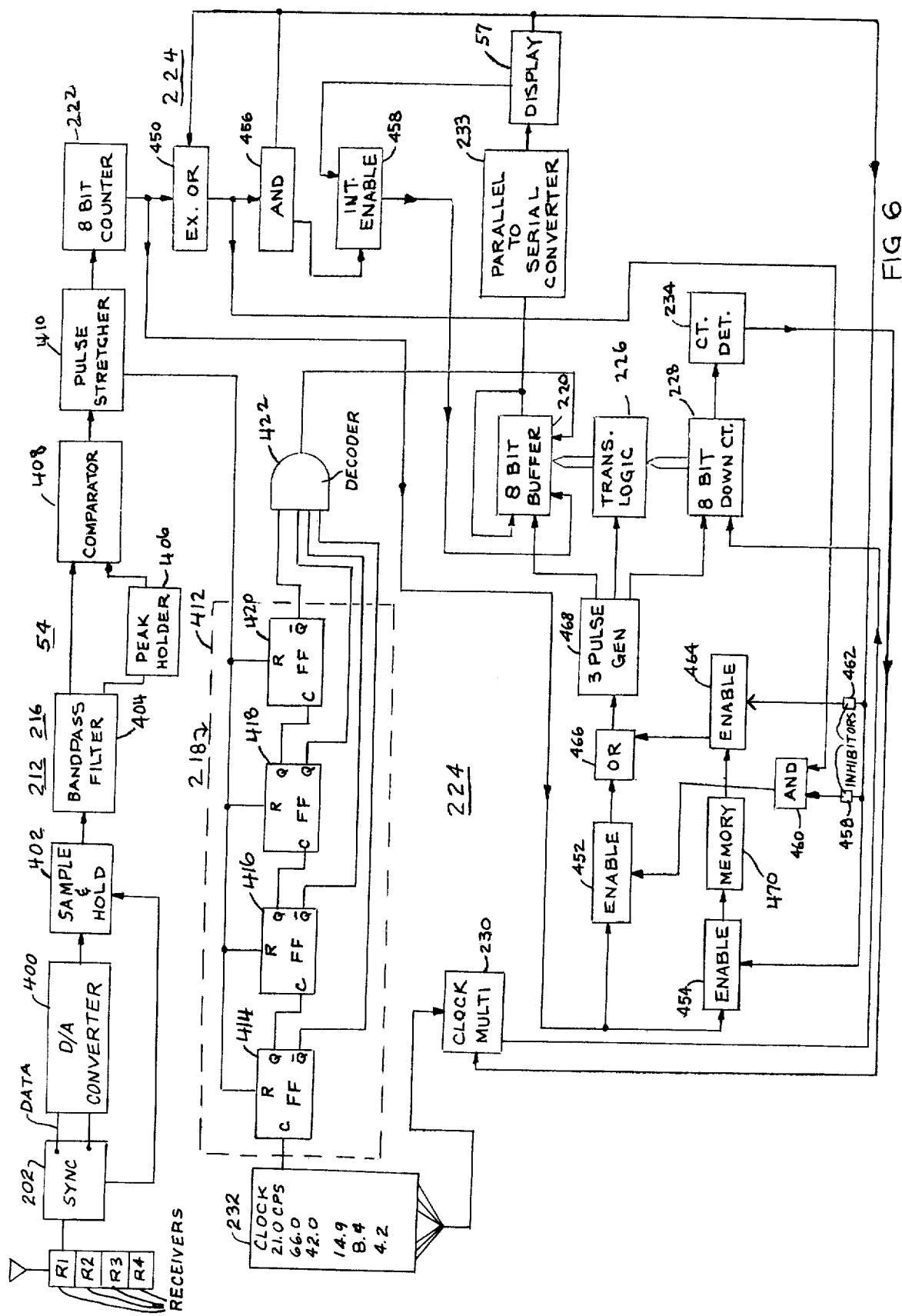
FIG. 6 is an electrical block diagram of that portion of the central monitor particularly relating to processing of rate data.

Heart rate detector 54 is generally illustrated in FIG. 3 and in greater detail in FIG. 6. It is divided into two sections, one being peak detector 212 and the other being heart rate counter 214. Heart rate counter 214 includes rate control 224 which is similar to analog control 212 shown in FIG. 5. Peak detector 212 in turn consists of peak sensor 216 and low rate detector 218. Peak sensor 216 functions to sense the peak of the QRS portion of an ECG waveform as shown in FIG. 8d. Low rate detector 218 operates to sense an extremely low heart rate and cause buffer 220 to partially reset to temporarily provide an approximate heart rate pending completion of a measurement of actual heart rate. Detector peaks are supplied by peak sensor 216 to eight bit counter 222 which thus provides a timing pulse for each QRS as sensed from the waveform. Heart rate counter 214 then functions to determine the heart rate or heart count by measuring the time required for eight heart beats. This measurement is accomplished by a straight line approximation in terms of the heart rate-/ECG curve illustrated in FIG. 7. This is the plot of frequency (pulses per minute) versus time for eight pulses or 8T. Thus the problem solved by heart rate counter 214 is stated in the equation: heart rate =60/T or 480/8T.

The curve of FIG. 7 plots the slopes or rates of clock frequencies as follows: 21.0, 66.0, 42.1, 27.15, 14.9, 8.4, and 4.2 cycles per second. As stated above the actual counting sequence is commenced by the application of a pulse from peak sensor 216 to eight bit pulse counter 22 indicating the occurrence of the peak of an ECG cycle. To more particularly examine the operation of heart rate detector 54, a reference is particularly made to FIG. 6.

Synchronizer 202 provides data and clock pulses to D to A convertor 400, which in turn supplies bits of analog data to sample and hold circuit 402. Sample and hold circuit 402 is also fed up-date pulse U which serves to trigger the acceptance or sampling inputs to this circuit during the time that data is accurate, which is for the period of the up-date pulse U, as shown in FIG. waveform 4c. Each bit of data is then held by sample and hold circuit 402 pending the receipt of the next bit of data to maintain available as an output, a continuous analog signal representation of the ECG condition being monitored. Essentially, sample and hold circuit 402 consists of a metal oxide semiconductor switch which applies pulses of ECG data to a capacitor. The output of sample and hold circuit 402 is fed to bandpass filter 404 which includes amplification and passive filtering to roll off response at two cycles and 20 cycles, and thus attenuating frequencies below two cycles and above 20 cycles. The result is a clean waveform following the QRS portion of the ECG waveform. In order to detect the peak of the waveform, one input of band pass filter 404 is fed to peak holder 406, which includes a differentiato and which provides a clamped output signal which is representative of the level of the peak of the QRS waveform less one volt. This output of peak holder 406 is fed to one input of comparator 408 together with a direct output of band pass filter 404. The output of comparator 408 which is the amplified difference between inputs which exist during the clamp period is a pulse as shown in FIG. waveform 8d and is representative of the time when a peak has occurred. This pulse is then fed to pulse stretcher 410, which provides an output as shown in waveform 8e which has a leading edge corresponding to the leading edge of the pulse shown in waveform 8d, but extends for a duration of 200 milliseconds as fixed by the circuit constants of pulse stretcher 410. The reason for providing the long pulse is to block the circuit to insure that eight bit counter 220 of heart rate counter 214 to provide the basis for the heart rate count. Heart rate counter 214 then measures the interval between eight counts as described above to provide an output of heart rate in terms of heart beats per minute. Low heart rate detector 218 provides a rapid indication that a dangerously low heart rate is sensed without the necessity of waiting for the occurrence of eight beats which is the normal detection period. (i.e., 32 seconds for bit line of 15 beats per minute). This is accomplished as follows: An 8.4 cycle clock pulse from clock pulse from clock oscillator source 232 to four stage counter 412 consisting of flip-flops 414, 416, 418 and 420. Thus when this counter reaches a count of 16, there is provided a pulse output from each stage to decoder 422 which then provides an output to reset the three upper value bits of eight bit buffer or holding register 460. This will immediately cause buffer 460 to register some value as represented by the remaining five lower value bit positions. And when fed through parallel to serial convertor 461 to display 57 will necessarily provide such a low value as will produce an alarm condition in the display as will be further described below. This action of low rate detector 218 will occur only if its operation is not interrupted by peak sensor 216 and an interruption will occur by reset of the flip-flops if the reset pulse is fed to each input or prior to a full 16 count occurring in low rate detector 218. The time required for this count is approximately 4 seconds or equal to a heart rate of 15 beats per minute. Thus if the actual heart rate being monitored drops so that there is a heart rate less than 15 beats some count is caused to appear in eight bit buffer 460 which is the sum of the five low bits in that register within two seconds. Thus a readout will of course vary but it cannot be more than 31 which, of course, to the observer of CRT 66 would indicate a critical condition. The actual count process is not stopped and the measured rate will occur at the end of eight beats.

Considering now the actual counting of heart rate, reference is made to FIG. 9 which illustrates the counting system and indicates that the counting sequence results in a rate curve formed by a series of rate lines which very closely approximate the ideal curve between count rates 66.0 and 4.2 which would be indicated by a line connecting the dots on FIG. 7. Counts outside of this range would be so extreme as to provide no useful information. As noted, initially down counter 228 is counted down at the rate of 21.0 cycles per second which is applied through clock multiplexer 230 which functions to switch the clock input to the 66.0 cycles per second count at a point on the curve where the 21.0 rate intersects what would be an ideal curve corresponding to a line through the dots on the chart. Counter 228 has been counted down by the 66.0 CPS clock frequency until count detector 234 detects the occurrence of count 759 whereupon it causes clock multiplexer 230 to switch to the 42.0 cycles per second clock frequency and so on down as indicated by the chart. The counting continues until eight bit counter 222 receives eight pulses, that is eight pulse periods have elapsed since counting commenced. At this point counter 222 sends a sync pulse to rate control 224 and the latter sends out three pulses to stop the count, reset eight bit buffer 220, transfer the present count up to buffer 220 and cause multiplexer 230 to reset and provide pulses at its initial 21.0 cycles per second rate, for the next count period which commences immediately. Count detector 234 (FIG. 3) which is not shown in detail, consists of a count detector to detect the respective counts: 207, 159, 127, 99, 73. The detection of each of the counts correspondingly switches the clock multiplexer 230 such that the next respective clock frequency is applied to eight bit counter 228. By the described method it has been found that an accuracy of plus or minus two counts per minute as achieved with updated outputs occurring once every eight beats.

In operation, display 57 routes an interrogate pulse to the detector of D1, then to the detector of C1, then in sequence to the analog and rate detectors D2, D3 and D4. In response, each of the data and rate detectors furnish data to parallel to serial convertor 233 which converts the digitized date to serial form and furnishes it to display 57.

The same problem of possible interference between transfer of data into and out of eight bit buffer 220 exists as with respect to eight bit buffer 208 of analog detector 52 and the same solution is employed. Accordingly, when eight bit counter 411 is full set, that is there has occurred eight input heart beat pulses, the up-date pulse U (waveform 4c) is applied from eight bit counter 411 to one input of EXCLUSIVELY OR circuit 450 and interrogate pulse I (d) from display 57 is applied to the other input of EXCLUSIVELY OR gate 450. Update pulses U are also supplied to enable sweep circuit 458 and 454. Interrogate pulses I (waveform 4d) are also supplied to one input of AND gate 456 and through inhibitor 458 to one input of AND gate 460. Interrogate pulses are also supplied through inhibitor 462 to enable circuit 464. Display clock pulses D (waveform 4e) which, as previously explained, consists of eight pulses followed within the period of interrogate pulse I, are supplied from display 57 as determined by display 57 are applied through interrogate enable circuit 458 to buffer 220. Buffer 220, an eight bit buffer, receives heart rate count through transfer logic 226 from eight bit down counter 228. If an interrogate pulse should arrive from display 57 at any time between the occurrence of successive up-date pulses U (waveform 4c) no interferring problem arises and thus operation is as follows. If only interrogate pulse I is applied to EXCLUSIVELY OR gate 450, it would appear at the output of EXCLUSIVELY OR gate 450 and be applied to one input and AND gate 456. Inhibitor 458 prevents it from being applied to AND gate 460. The interrogate pulse is also applied to the other input of AND gate 456 which in turn provides an enable input to interrogate enable 458 to permit the passage of a burst of eight clock pulses D from display 57 to eight bit buffer 220 which causes the stored data therein, representing the last measured heart rate, to be clocked out to display 58.

We will next assume a condition wherein there is interference or overlap between the occurrence of an interrogate pulse I and an up-date pulse U wherein the up-date pulse is received first. Thus, up-date pulse U is applied to one input of EXCLUSIVELY OR gate 450 at a time when no interrogate pulse is applied to the other input. Thus up-date pulse U would appear as an output of EXCLUSIVELY OR gate 450 and as an input to AND gates 456 and 460. Initially, before an interrogate pulse is applied to inhibitor 458, AND gate 460 is operated and in turn so is enable circuit 452 to permit up-date pulses used to pass through OR gate 466 to three pulse generator 468 and perform the following operations. Input pulse to three pulse generator 468 indicates that there has occurred eight heart beats since the last pulse received by generator 468 and thus that a new count is to be registered. The three pulses from three pulse generator 468 are then supplied to eight bit down counter 228, which stops the count into it from multiplexer 230, where supply to eight buffer 220 is reset, and they are supplied to transfer logic 226 which transfers the count from down counter 228 up to eight bit buffer 220 and thus a new count is registered in buffer 220. This requires only 3 microseconds and thus it will be noted that this up-date will be completed prior to the occurrence of the first of the eight clock pulses (waveform 4e). There is 6 microseconds time lapse after the beginning of interrogate pulse I until the first clock pulse arrives and we have stated that the up-date process is only 3 microseconds in duration and had commenced prior to interrogate pulse.

Next, to further illustrate that the up-date sequence does not interfere with the process of clock out of data from buffer register 220, it is to be noted that as soon as the interrogate pulse does arrive and the up-date pulse ends, EXCLUSIVELY OR gate 450 is operated and this causes AND gate 456 to be operated and it in turn operates interrogate enable 458 so that clock pulses are permitted through interrogate enable 458 to buffer 220 and the data is clocked out to display 257. Since there is a 6 microsecond delay between the arrival of interrogate pulse and the first of the clock pulses, clock out can occur only after up-date has been completed.

We will now assume the third possible condition and that is where interrogate pulse I (waveform 4d) has arrived first and up-date pulse U (waveform 4c) arrives sometime thereafter and during interrogate pulse I. Initially and with only interrogate pulse I present, output of EXCLUSIVELY OR gate 450 is applied to AND gate 456 and AND gate 460. Inhibitor 464 through which enable 464 is operated prevents the operation of enable circuit 464 and any up-date from memory circuit 470 to operate three pulse generator 448. However, at the end of interrogate pulse I and with no input to inhibitor 462, the latter is no longer inhibited and enable circuit 464 is energized to pass the up-date pulse from memory circuit 470 through OR I gate 466 to three pulse generator 468 which then accomplishes update as described above. In the meantime and during interrogate pulse I, interrogate enable circuit 458 is operated by AND gate 456 and display clock pulses D are fed through buffer 220 and the data stored therein is blocked out to display 57. Thus, in instances where an interrogate pulse requesting data occurs first and an up-date pulse indicating time for up-date of data occurs during interrogating pulse, up-dating is inhibited during the interrogate period but is accomplished immediately at the end of the interrogate period. Thus there is no loss of rate data, up-dating occurring once for each new word of data received.

What is claimed is:

1. A physiological monitoring system comprising:

A. first, second and third electrodes adapted to be positioned on the body of a patient;
B. a first amplifier adapted to amplify the output of said first electrode and assecond amplifier adapted to amplify the output of said second electrode;
C. an electrical system ground potential point common to said amplifiers;
D. bias means adapted to apply a fixed bias to said third electrode and a patient with respect to said ground potential point of said system;
E. sample and hold means responsive to the outputs of said first and second amplifiers with respect to said third electrode for converting a balanced output to a single ended output of pulses of a predetermined rate and of an amplitude proportional to the input of said sample and hold means;
F. analog to digital conversion means for encoding output pulses of said sample and hold means into discrete binary encoded words;
G. transmission means for transmitting the output of said analog to digital conversion means for display at a remote location; and
H. display means responsive to said output of said analog to digital conversion means for decoding electrical signals sensed by said first, second and third electrodes as physhological data and displaying said data.

* * * * *